(12) United States Patent
Borot et al.

(10) Patent No.: US 11,207,140 B2
(45) Date of Patent: Dec. 28, 2021

(54) ULTRASOUND-ENABLED INVASIVE MEDICAL DEVICE AND METHOD OF MANUFACTURING AN ULTRASOUND-ENABLED INVASIVE MEDICAL DEVICE

(71) Applicant: GE Precision Healthcare LLC, Wauwatosa, WI (US)

(72) Inventors: Maxence Borot, Antibes (FR); Flavien Daloz, Biot (FR); Edouard Da Cruz, Nice (FR); Coraly Cuminatto, Le Cannet (FR); Frederic Lanteri, Le Cannet (FR); Giandonato Stallone, Nice (FR); Alexandre Gilibert, Valbonne (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 260 days.

(21) Appl. No.: 16/718,585

(22) Filed: Dec. 18, 2019

(65) Prior Publication Data
US 2021/0186618 A1 Jun. 24, 2021

(51) Int. Cl.
*A61B 34/20* (2016.01)
*A61B 8/12* (2006.01)
*A61B 17/34* (2006.01)
*A61F 2/82* (2013.01)
*A61M 25/01* (2006.01)
(Continued)

(52) U.S. Cl.
CPC .............. *A61B 34/20* (2016.02); *A61B 8/12* (2013.01); *A61B 8/4494* (2013.01); *A61B 17/3403* (2013.01); *A61F 2/82* (2013.01); *A61M 25/0102* (2013.01); *A61M 25/0108* (2013.01); *A61B 2017/3413* (2013.01); *A61B 2034/2063* (2016.02); *A61F 2250/0096* (2013.01); *A61N 1/05* (2013.01)

(58) Field of Classification Search
CPC ........ A61B 17/3403; A61B 2017/3413; A61B 2034/2063; A61B 2090/3784; A61B 34/20; A61B 5/24; A61B 8/08; A61B 8/12; A61B 8/4494; A61F 2250/0096; A61F 2/82; A61M 25/0102; A61M 25/0108; A61N 1/05; A61N 1/08
See application file for complete search history.

(56) References Cited

U.S. PATENT DOCUMENTS 7,108,894 B2 9/2006 Renn
2017/0288638 A1 10/2017 Wildes
(Continued)

*Primary Examiner* — Michael T Rozanski

(57) ABSTRACT

An ultrasound-enabled invasive medical device and a method of manufacturing the ultrasound-enabled invasive medical device. The ultrasound-enabled invasive medical device includes an invasive medical device, an electrical trace deposited either directly on the surface of the invasive medical device or onto an insulating layer covering at least a portion of the surface of the invasive medical device, where the electrical trace is deposited during an additive manufacturing process. The ultrasound-enabled invasive medical device includes an ultrasound transducer assembly attached to the invasive medical device and electrically connected to the electrical trace, and a transducer support structure attached to the invasive medical device, where the transducer support structure defines a nest that is adapted to receive the ultrasound transducer assembly.

34 Claims, 12 Drawing Sheets

(51) Int. Cl.
*A61B 8/00* (2006.01)
*A61N 1/05* (2006.01)

(56) References Cited

U.S. PATENT DOCUMENTS

| | | |
|---|---|---|
| 2018/0169701 A1 | 6/2018 | Daloz |
| 2018/0175278 A1 | 6/2018 | Daloz |
| 2020/0205779 A1* | 7/2020 | Khalaj ................ A61B 8/4444 |

* cited by examiner

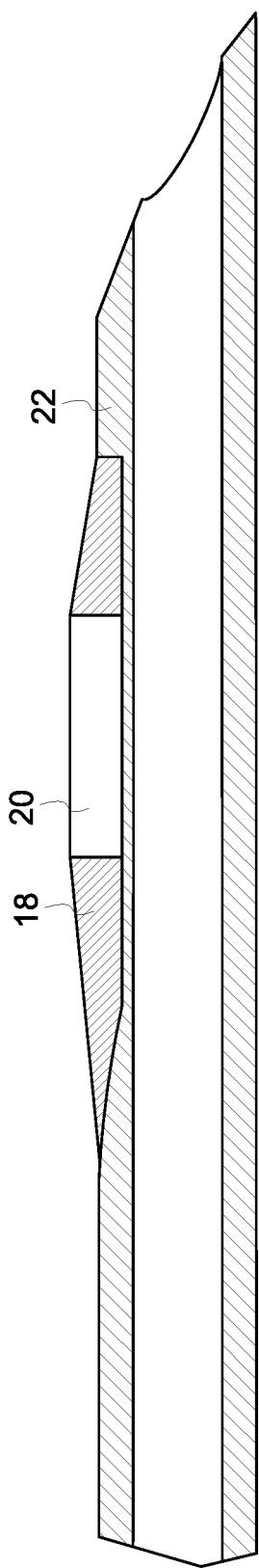

ULTRASOUND-ENABLED INVASIVE MEDICAL DEVICE AND METHOD OF MANUFACTURING AN ULTRASOUND-ENABLED INVASIVE MEDICAL DEVICE

BACKGROUND OF THE INVENTION

The subject matter disclosed herein relates generally to an ultrasound-enabled invasive medical device and a method of manufacturing an ultrasound-enabled invasive medical device.

It is desirable to attach an ultrasound transducer assembly including one or more ultrasound transducer elements to an invasive medical device for numerous reasons. For instance, the ultrasound transducer assembly may be used to acquire ultrasound images from the current location of the invasive medical device, the ultrasound transducer assembly may be used to provide therapy to one or more regions of the patient's body or the ultrasound transducer assembly may be used to help guide the invasive medical device. The ultrasound transducer assembly may be used like a conventional ultrasound probe for applications where ultrasound images are desired. For applications where the ultrasound transducer assembly is used for guidance, the ultrasound transducer assembly may transmit and/or receive ultrasound signals from one or more additional ultrasound elements in order to identify the position of the invasive medical device with respect to the one or more additional ultrasound elements.

It is often desirable to minimize the overall size of an invasive medical device since it will be introduced into the body of a patient. Too large of a size may decrease one or both of patient safety and patient comfort. Conventional ultrasound probes rely on an interconnect in order to control the ultrasound transducer assembly and/or receive signals from the ultrasound transducer assembly. Electrically conductive wires, printed circuit boards (PCBs) and flexible printed circuit boards (flex PCBs) are typically used as interconnects in conventional ultrasound probes. The use of conventional interconnects, such as wires, PCBs and flex PCBs, is challenging for invasive medical devices. For example, flex PCB manufacturing is oftentimes inconsistent and there may be significant variation between individual flex PCBs. Additionally, it can be challenging for the manufacturer to handle a flex PCB without breaking one of more of the electrical traces on the flex PCB. Additionally, it is difficult to manage small gauge wires on an invasive medical device with a small form-factor. In order to minimize the risk of breaking a conventional interconnect, it is necessary for the manufacturing process to require a large number of manually-performed steps. Additionally, the manual nature of the assembly typically results in an assembly process that focuses on only one individual invasive medical device at a time. This increases the time to manufacture each device, which, in turn, increases the per-unit cost of the completed device.

In addition, due to the small size of some invasive devices and the even smaller size of the ultrasound transducer assemblies that are attached to the invasive medical device in order to form an ultrasound-enabled invasive medical device, it is very challenging to accurately position the ultrasound transducer assembly on the invasive medical device. Accurate positioning of the ultrasound transducer assembly on the invasive medical device is key for the ultrasound-enabled invasive medical device to reliably perform its intended function.

Therefore, for at least the reasons discussed above, there exists a need for an improved ultrasound-enabled invasive medical device and an improved method for manufacturing an ultrasound-enabled invasive medical device.

BRIEF DESCRIPTION OF THE INVENTION

In an embodiment, an ultrasound-enabled invasive medical device includes an invasive medical device, an electrical trace deposited either directly onto a surface of the invasive medical device or onto an insulating layer covering at least a portion of the surface of the invasive medical device, wherein the electrical trace is deposited during an additive manufacturing process, an ultrasound transducer assembly attached to the invasive medical device and electrically connected to the electrical trace, wherein the ultrasound transducer assembly includes at least one ultrasound transducer element, and a transducer support structure attached to the invasive medical device and positioned over at least a portion of the electrical trace, wherein the transducer support structure defines a nest that is adapted to receive the ultrasound transducer assembly.

In an embodiment, a method of manufacturing an ultrasound-enabled invasive medical device includes depositing an electrical trace either directly onto a surface of an invasive medical device or onto an insulating layer covering at least a portion of the surface of the invasive medical device, wherein said depositing the electrical trace is performed via an additive manufacturing process. The method includes attaching a transducer support structure to the invasive medical device, wherein the transducer support structure is positioned over at least a portion of the electrical trace, wherein the transducer support structure defines a nest, and positioning an ultrasound transducer assembly within the nest defined by the transducer support structure and electrically connecting the ultrasound transducer assembly to the electrical trace, wherein the ultrasound transducer assembly includes at least one ultrasound transducer element.

BRIEF DESCRIPTION OF THE DRAWINGS

FIG. 2F is a sectional view of an ultrasound-enabled invasive medical device in accordance with an embodiment;

DETAILED DESCRIPTION OF THE INVENTION

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
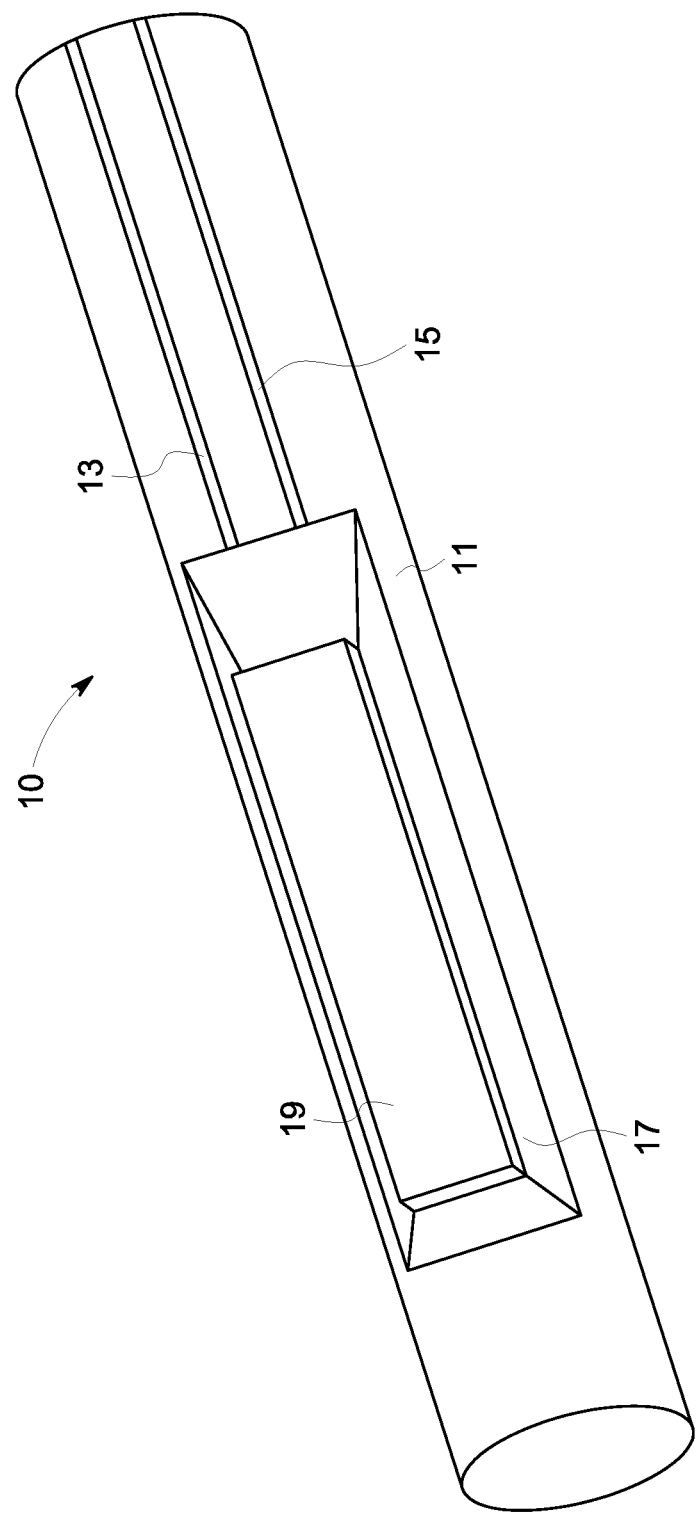
FIG. 1 is schematic representation of an ultrasound-enabled invasive medical device in accordance with an exemplary embodiment.

FIG. 1 is a schematic representation of an ultrasound-enabled invasive medical device 10 in accordance with an embodiment. The ultrasound-enabled invasive medical device 10 includes an invasive medical device 11, a first electrical trace 13, a second electrical trace 15, a transducer support structure 17, and an ultrasound transducer assembly 19. The invasive medical device 10 is schematically represented as a cylinder in FIG. 1. The invasive medical device 10 may be any type of medical device intended to be used inside a patient's body. For example, the invasive medical device 10 may be a catheter, an electrode, a stent, a needle, or any other medical device that is adapted to be used inside a patient. The ultrasound-enabled invasive medical device 10 may also include a connector adapted to attach the ultrasound-enabled invasive medical device 10 to a processor or medical device located outside of the patient during the procedure. The ultrasound-enabled invasive medical device 10 shown in FIG. 1 does not illustrate the connector.

The first electrical trace 13 and the second electrical trace 15 are made of an electrically conductive material that is deposited on either a surface of the invasive medical device 11 or on an insulting layer covering at least a portion of the surface of the invasive medical device 11. The first electrical trace 13 and the second electrical trace 15 are deposited by an additive manufacturing process. The electrically conductive material used to form the first electrical trace 13 and the second electrical trace 15 may be any electrically conductive material configured to be deposited via an additive manufacturing process. For example, the first electrical trace 13 and the second electrical trace 15 may be made of metals, such as silver, aluminum, copper, gold and/or alloys including silver, aluminum, copper or gold. Additionally, the first electrical trace 13 and the second electrical trace 15 may be made of composite materials, such as a plastic doped with conductive particles. The first electrical trace 13 and the second electrical trace 15 may be made from single crystal nano particles. The single crystal nano particles may be any conductive material, such as silver or copper. Additional details about the manufacturing process will be described hereinafter.

The ultrasound transducer assembly 19 includes at least one ultrasound transducer element and may be either a single-element array including only a single ultrasound transducer element, or the ultrasound transducer assembly 19 may be a multi-element array including 2 or more ultrasound transducer elements. Each of the ultrasound transducer elements may be a piezoelectric (PZT) element, a capacitive micromachined ultrasonic transducer (CMUT) element, a micromachined ultrasound transducer (MUT) element, or the ultrasound transducer elements in the ultrasound transducer array may be a combination of PZT, CMUT and/or MUT elements. Only two electrical traces are illustrated in the embodiment shown in FIG. 1, but some embodiments may have only a single electrical trace while still other embodiments may have more than two electrical traces. It is necessary to have two electrical connections to each ultrasound transducer element that is configured to be individually controlled. Each individually controllable ultrasound transducer element needs one conductive path to carry a control signal and a second conductive path for a ground return. Embodiments, such as the one shown in FIG. 1, may use two separate electrical traces: one to carry the control signal and another to function as the ground return. In other embodiments, such as those where the invasive medical device is conductive, it is possible to electrically isolate the electrical trace from the invasive medical device and use the invasive device to either carry the control signal or perform as the ground return. An exemplary embodiment using the invasive medical device as a conductive path will be described in detail hereinafter with respect to FIGS. 8A and 8B.

The transducer support structure 17 is shaped to define a nest, and the nest is adapted to receive the ultrasound transducer assembly 19. The nest is not easy to see in FIG. 1 because the ultrasound transducer assembly 19 is positioned in the nest defined by the transducer support structure 17. The first electrical trace 13 and the second electrical trace 15 are both connected to the ultrasound transducer assembly 19. The first electrical trace 13 may be configured to carry the control signal while the second electrical trace 15 may be adapted to function as the ground return. Or the first electrical trace 13 may be adapted to function as the ground return while the second electrical trace 15 is configured to carry the control signal.

Figure 2A:
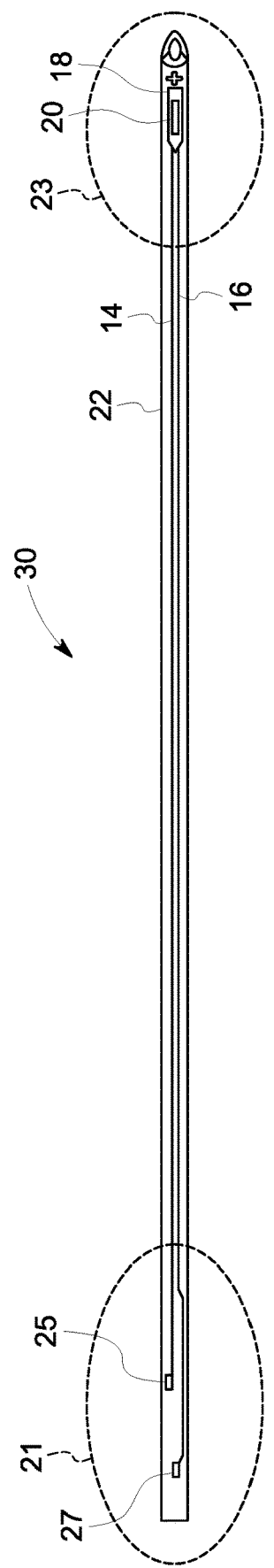
FIG. 2A is a top view of an ultrasound-enabled invasive medical device in accordance with an embodiment.

FIG. 2A is a top view of an ultrasound-enabled invasive medical device 30 where the invasive medical device is a needle 22. The ultrasound-enabled invasive medical device 30 includes a first electrical trace 14, a second electrical trace 16, a transducer support structure 18, and an ultrasound transducer assembly 20. The ultrasound-enabled invasive medical device 30 includes a proximal end 21 and a distal end 23. The ultrasound-enabled invasive medical device 30 also includes a first electrical pad 25 and a second electrical pad 27. The first electrical pad 25 and the second electrical pad 27 are configured to electrically connect the ultrasound-enabled medical device 30 to an external device that is configured to provide a control signal to drive the ultrasound transducer assembly 20.

Figure 2B:
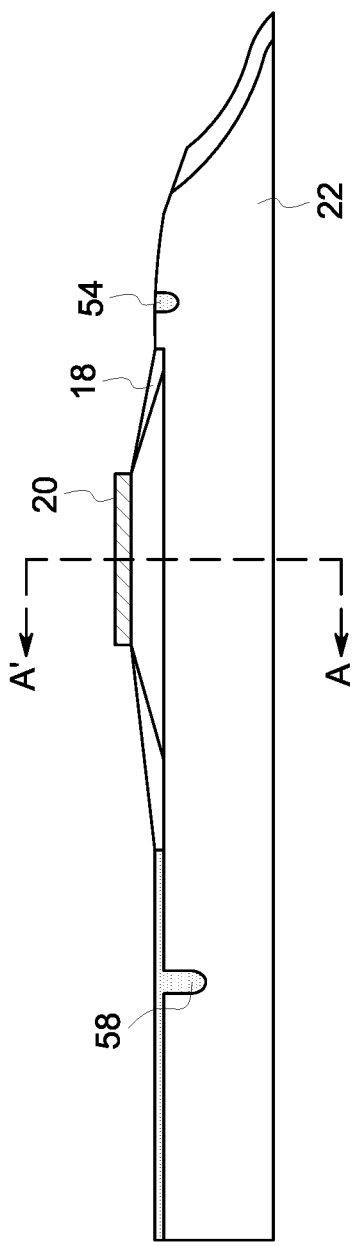
FIG. 2B is a side view of the distal end of an ultrasound-enabled invasive medical device in accordance with an embodiment.
Figure 2C:
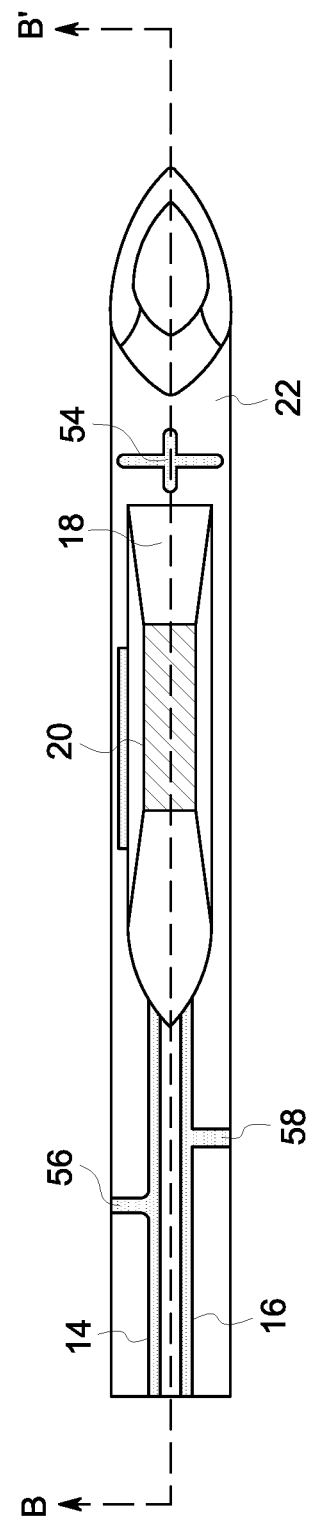
FIG. 2C is a top view of the distal end of an ultrasound-enabled invasive medical device in accordance with an embodiment.

FIG. 2B is a side view of the distal end 23 of the ultrasound-enabled medical device 30 and FIG. 2C is a top view of the distal end 23 of the ultrasound-enabled medical device 30 in accordance with an exemplary embodiment.

Figure 2D:
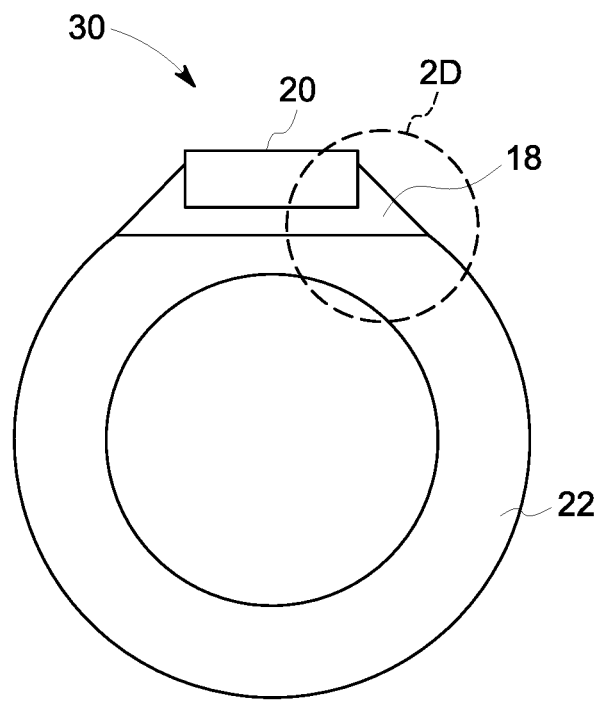
FIG. 2D is a sectional view of an ultrasound-enabled invasive medical device in accordance with an embodiment.

FIG. 2D is a sectional view of the ultrasound-enabled invasive medical device 30 along the dashed line A-A' shown in FIG. 2B.

Figure 2E:
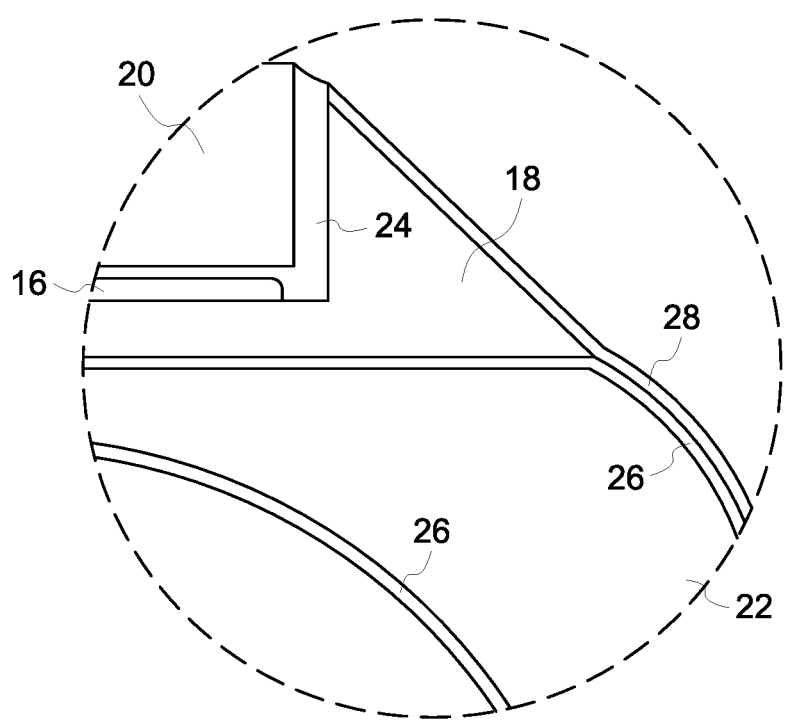
FIG. 2E is a portion of the sectional view shown in FIG. 2D that has been enlarged for magnification purposes in accordance with an embodiment.

FIG. 2E is a portion of the sectional view shown in FIG. 2D that has been enlarged for magnification purposes. FIG. 2E shows an adhesive 24 used to attach the ultrasound transducer assembly 20 to the transducer support structure 18 and the needle 22. FIG. 2E also shows a first insulating layer 26 and a second insulating layer 28. The first insulating layer 26 and the second insulating layer 28 will be described hereinafter. FIG. 2F is a sectional view along line B-B'.

Figure 3:
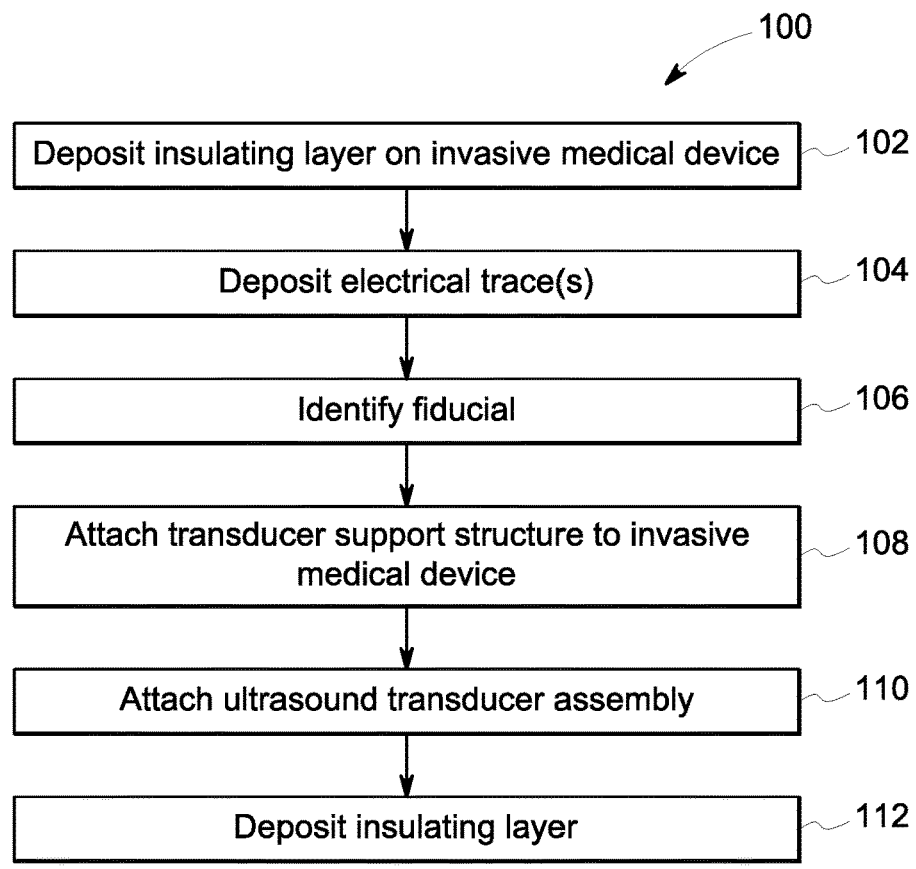
FIG. 3 is a flow chart of a method in accordance with an exemplary embodiment.

FIG. 3 is a flow chart showing a method 100 in accordance with an exemplary embodiment. The individual blocks of the flow chart represent steps that may be performed in accordance with the method 100. Additional embodiments may perform the steps shown in a different sequence and/or additional embodiments may include additional steps not shown in FIG. 3. The technical effect of the method 100 is the manufacturing of an ultrasound-enabled invasive medical device. The method 100 will be described in detail with respect to the manufacture of the ultrasound-enabled invasive medical device 30, previously described with respect to FIGS. 2A-2F. It should be appreciated by those skilled in the art that the method 100 may be used in the manufacture of ultrasound-enabled invasive medical devices other than the ultrasound-enabled invasive medical device 30 in accordance with various embodiments.

At step 102, an insulating layer is deposited on the invasive medical device, such as the needle 22 according to an exemplary embodiment. The insulating layer may be any insulating material according to various embodiments. According to exemplary embodiments, the insulating layer may be a vapor-deposited poly polymer such as Parylene C or polydimethylsiloxane (PDMS).

Figure 4:
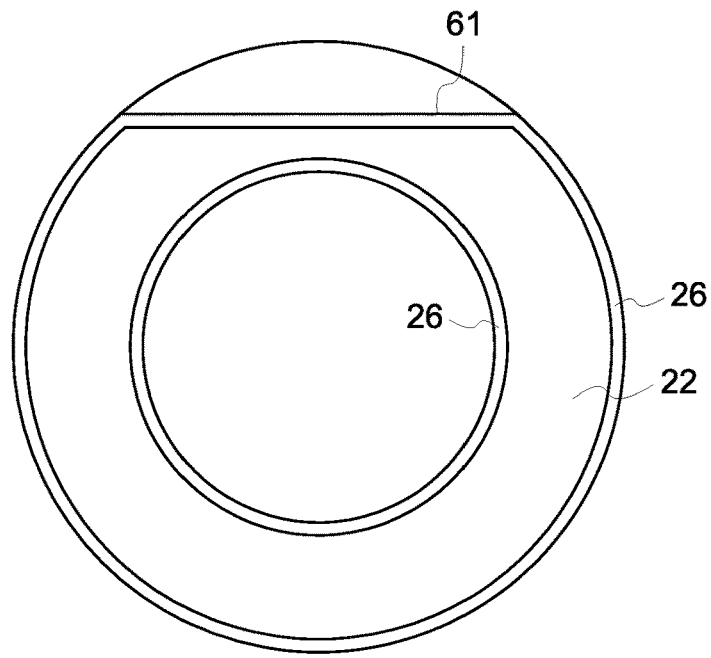
FIG. 4 is a sectional view of a needle in accordance with an exemplary embodiment.

FIG. 4 is a sectional view of the needle 22 along dashed line A-A' (shown in FIG. 2B) after it has been coated with an insulating layer 26 at step 102. The insulating layer 26 may be deposited though a vacuum-based process, a chemical vapor deposition process, a spin coating process, a mechanical dipping process, or insulating layer 26 may be applied through an additive manufacturing process such as ink-jetting, aerosol jet printing or dispensing. According to an exemplary embodiment, the insulating layer 26 may be deposited on all or a portion of the surface of the needle 22 through a vapor deposition process.

The insulating layer 26 may be deposited on all of the invasive medical device, such as the needle 22, or the insulating layer 26 may be deposited on just a portion of the invasive medical device. For embodiments where it is desirable to deposit the insulating layer on just a portion of the invasive medical device, a mask may be used in order to keep some of the invasive medical device uninsulated.

At step 104, one or more electrical traces are deposited on either the surface of the invasive medical device or on the insulating layer 26 deposited on the surface of the invasive medical device. According to embodiments where the invasive medical device 11 is an electrical insulator, or at least the portion of the invasive medical device 11 where the electrical traces will be deposited is an electrical insulator, it may not be necessary to add an insulating layer. For embodiments where the invasive medical device is not electrically conductive, one or more electrical traces may be deposited directly on the surface of the invasive medical device 11. Therefore, step 102 may be skipped according to some embodiments.

Figure 5A:
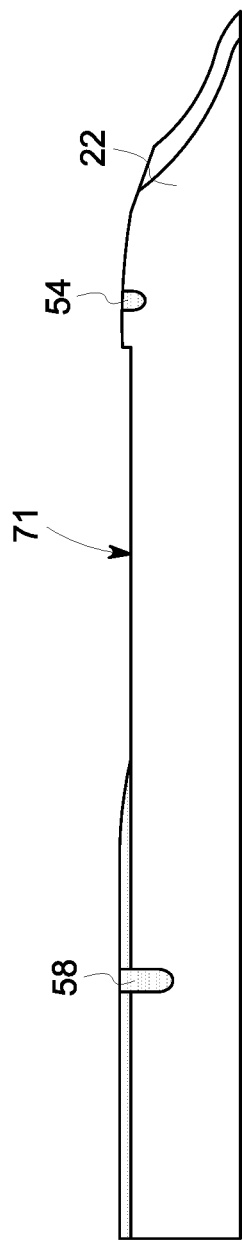
FIG. 5A is a side view of a needle in accordance with an exemplary embodiment.
Figure 5B:
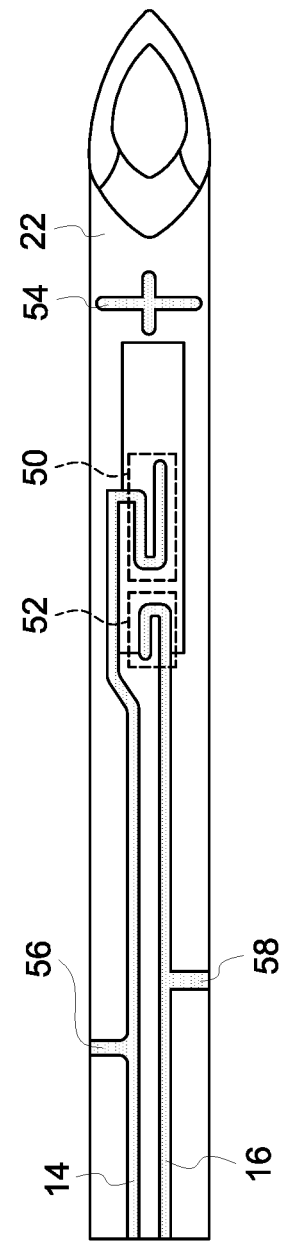
FIG. 5B is a top view of a needle in accordance with an exemplary embodiment.

FIG. 5A is a side view of the needle 22 and FIG. 5B is a top view of the needle 22 in accordance with an embodiment. Both FIG. 5A and FIG. 5B show the needle 22 without either the ultrasound transducer assembly 20 or the transducer support structure 18 in order to more clearly show the first electrical trace 14 and the second electrical trace 16. FIGS. 5A and 5B represent the needle 22 after the electrical traces have been deposited during step 104.

According to the exemplary embodiment shown in, for example, FIGS. 2A-2F, the insulating layer 26 is deposited on the surface of the needle 22, and the first electrical trace 14 and the second electrical trace 16 are deposited on the insulating layer 26. The first electrical trace 14 and the second electrical trace 16 are deposited through an additive manufacturing process, such as ink-jetting, a spin coating process, aerosol jet printing, or dispensing. The first electrical trace 14 and the second electrical trace 16 are both visible in FIG. 5B. The first electrical trace 14 includes a first contact portion 50 and a second contract portion 52. The first contact portion 50 is configured to be the point of electrical connection between the ultrasound transducer assembly 20 and the first electrical trace 14; and the second contact portion 52 is configured to be the point of electrical connection between the ultrasound transducer assembly 20 and the second electrical trace 16. Other embodiments may use contact portions that are shaped differently than the first contact portion 50 or the second contact portion 52. One or both of the first electrical trace 14 and the second electrical trace 16 may be shaped to form one or more fiducials. The embodiment shown in FIGS. 5A and 5B includes a first fiducial 54, a second fiducial 56 and a third fiducial 58. Each fiducial (54, 56, 58) or the combination of fiducials (54, 56, 58) is shaped to be identified quickly and reliably by an optical camera system connected to a processor with a pattern recognition system. While the second fiducial 56 and the third fiducial 58 are integral portions of the first electrical trace 14 and the second electrical trace respectively, the first fiducial 54 is separate from either of the electrical traces. Other embodiments may generate one or more fiducials from materials other than the conductive material used to form the electrical traces.

At step 106, a fiducial (54, 56, 58) is identified with a processor and an optical camera system. The processor and optical camera system use the fiducial to make sure the transducer support structure 18 is properly positioned with respect to the first electrical trace 14 and the second electrical trace 16 during step 108

At step 108 the transducer support structure 18 is attached to the invasive medical device 12. As discussed previously, the transducer support structure 18 may be attached to an insulating layer, such as insulating layer 26, added to the invasive medical device 12 during step 102 or the transducer support structure 18 may be directly attached to the surface of the invasive device 12. According to an exemplary embodiment, the transducer support structure 18 may be attached to the insulating layer 26 covering at least a portion of the needle 22.

Figure 6A:
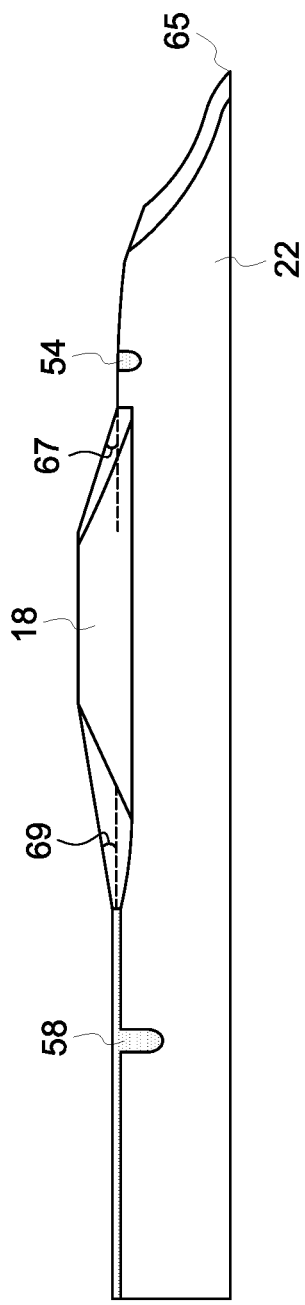
FIG. 6A is a side view of a needle and a transducer support structure in accordance with an exemplary embodiment.
Figure 6B:
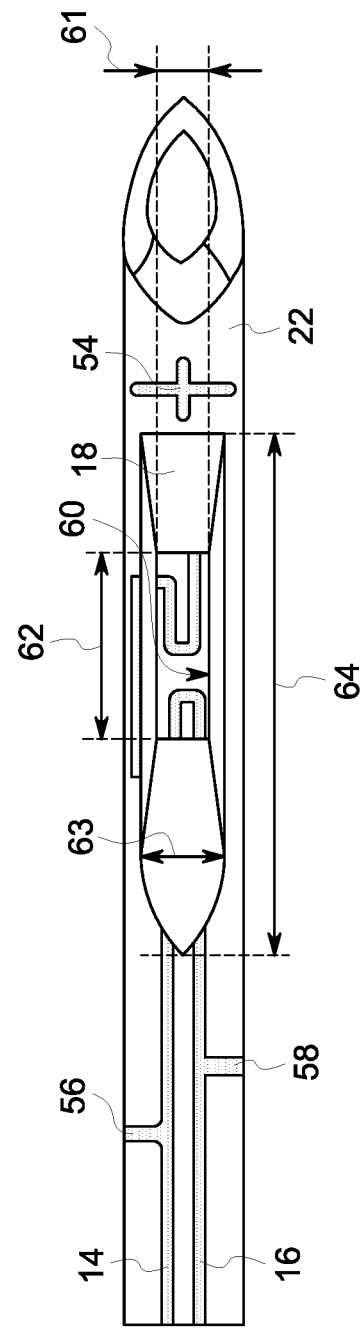
FIG. 6B is a top view of a needle and a transducer support structure in accordance with an exemplary embodiment.

According to an embodiment, the transducer support structure 18 may be manufactured separately, through a process such as molding or micro-molding, and then laminated to either the invasive medical device 12 or to the insulating layer 26 covering at least a part of the invasive medical device 12. FIG. 6A is a side view of the needle 22 after the transducer support structure 18 has been attached to the needle 22. FIG. 6B is a top view of the needle 22 after the transducer support structure 18 has been attached to the needle 22. FIG. 6B clearly show the nest 60 defined by the transducer support structure 18. According to an embodiment, the nest 60 may have dimensions that are between 100% and 200% that of the ultrasound transducer assembly 20. For example, according to an exemplary embodiment where the ultrasound transducer assembly 20 has a width of 200 μm and a length of 1000 μm, an inner width 61 of the nest 60 may be 350 μm and an inner length 62 of the nest 60 may be 1000 μm. An overall width 63 of the nest 60 may be 690 μm and an overall length 64 of the nest 60 may be 3100 μm. The ultrasound transducer assembly 20 includes a first ramp angle 67 of 10 degree and a second ramp angle 69 of 6 degrees. The first ramp angle 67 and the second ramp angle 69 are designed to allow for a smoother insertion of the ultrasound-enabled invasive medical device 30 into the patient. The first ramp 67 and the second ramp angle 69 help to streamline the ultrasound transducer assembly 20 so that it does not unintentionally abrade or damage additional tissue during the insertion or removal of the ultrasound-enabled invasive medical device 30. Other embodiments may use different a different first ramp angle 67 and/or a different second ramp angle 69. For example, the first ramp angle 67 may be between 5 degrees and 45 degrees according to various embodiments. The second ramp angle 69 may be between 5 degrees and 45 degrees according to various embodiments. The first ramp angle 67 is steeper than the second ramp angle 69 in the embodiment shown in FIG. 6B because it is desirable to have the ultrasound transducer assembly 20 closer to a distal end 23 of the needle. Positioning the ultrasound transducer assembly 20 close to the distal end 23 of the needle is desirable for more accurate localization of the needle 22 during interventional procedures. It should be appreciated that the dimensions described above are for one particular embodiment and that the dimensions of the nest 60 and the transducer support structure 18 may be adjusted based on the dimensions of the ultrasound transducer assembly and/or according to various embodiments. The nest 60 is adapted to receive the ultrasound transducer assembly 20. The placement and lamination of the transducer support structure 18 may be performed as part of an automated process, such as a pick-and-place process according to embodiments. For example, the invasive medical device, such as the needle 22, may be held in a fixture to ensure the accurate placement of the transducer support structure 18 with respect to the electrical traces (14, 16). Or, an optical camera system in conjunction with a processor may be used to identify one or more fiducials, such as the first fiducial 54, the second fiducial 56, or the third fiducial 58, and guide the placement of the transducer support structure 18 to a predetermined position with respect to the one or more fiducials (54, 56, 58).

According to another embodiment, the transducer support structure 18 may be deposited onto the invasive medical device 12 or onto the insulating layer 26 covering at least a portion of the invasive medical device 12 through an additive manufacturing process. For example, the transducer support structure 18 may be deposited through a process such as ink-jetting, aerosol jet printing, spin coating, or dispensing. The transducer support structure 18 may be deposited by an additive manufacturing process or manufactured separately and then laminated to the needle 22. As described previously, the transducer support structure 18 shown in FIG. 7 may be either directly attached to the needle 22 or it may be attached to the insulating layer 26 covering the surface of the needle 22. Since the ultrasound transducer assembly 20 is not shown in FIGS. 5A and 5B, it is possible to visualize the first electrical trace 14, the second electrical trace 16, and the fiducials (54, 56, 58).

The transducer support structure 18 defines the nest 60 that is configured to receive the ultrasound transducer assembly 20. The nest 60 is dimensionally slightly larger than the size of the ultrasound transducer assembly 20. For example, the nest 60 may have a length and a width that are between 50 μm and 500 μm larger than a length and a width of the ultrasound transducer assembly 20. According to an embodiment, a height of the transducer support structure 18 is at least 80% of the height of the transducer assembly 20. According to other embodiments, the height of the transducer support structure 18 is at least 60% of the height of the transducer assembly 20; according to other embodiments, the height of the transducer support structure 18 is at least 70% of the height of the transducer assembly 20; and according to other embodiments, the height of the transducer support structure 18 is at least 100% of the height of the transducer assembly 20. The transducer support structure 18 ensures that the ultrasound transducer assembly 20 is accurately positioned with respect to the electrical traces, such as the first electrical trace 14 and the second electrical trace 16. Additionally, using the transducer support structure 18 results in a more accurate placement and a more reliable attachment of the ultrasound transducer assembly 20 to the needle 22. The transducer support structure 18 helps to control the adhesive, such as glue or epoxy, that is used to encapsulate the ultrasound transducer assembly 20. The transducer support structure contains the adhesive that is used for the encapsulation process. Both of these improvements make it easier to produce the ultrasound-enable invasive medical device using automated techniques.

At step 110, the ultrasound transducer assembly 20 is positioned within the nest 60 defined by the transducer support structure 18 and attached to the invasive medical device, such as needle 22. According to an embodiment, an adhesive, such as epoxy may be placed within the nest 60 prior to attaching the ultrasound transducer assembly 20. The nest 60 defined by the transducer support structure 18 advantageously contains the adhesive, which otherwise might run off a small invasive medical device such as a needle. After adding the adhesive, the ultrasound transducer assembly 20 is positioned within the nest 60 defined by the transducer support structure 18. After the adhesive has cured, the ultrasound transducer assembly 20 is secured to the needle 12. The nest 60 defined by the transducer support structure 18 contains the adhesive before placement of the ultrasound transducer assembly and ensures better control of the encapsulation process—i.e., the process of securing the ultrasound transducer assembly 20 with the adhesive. As the ultrasound transducer assembly 20 is positioned in the nest 60, the adhesive will be displaced and spread out to the sides of the ultrasound transducer assembly 20. The nest 60, however, contains the adhesive and prevents it from spreading beyond the walls of the transducer support structure 18 defining the nest 60. The adhesive then travels up the sides of the ultrasound transducer assembly 20 adjacent to the walls of the transducer support structure 18. According to an embodiment, the ultrasound transducer assembly 20 may be attached to the needle 22 automatically via a pick-and-place process. The pick-and-place process may, for instance, entail using a pick-and-place robot to grab various components of the ultrasound-enabled invasive medical device and position the individual components on the invasive medical device to assemble the completed ultrasound-enabled invasive medical device. For instance, the pick-and-place robot may attach the transducer support structure 18 to either the needle 22 or to the insulating layer 26 covering the needle 12. The pick-and-place robot may automatically dispense the adhesive within the nest 60, and the pick-and-place robot may then place the ultrasound transducer assembly 20 within the nest 60 after the adhesive has been applied. In addition to helping with the encapsulation process, the nest 60 defined by the transducer support structure 18 helps ensure an accurate placement of the ultrasound transducer assembly with respect to both the needle 22 and with respect to the electrical traces (14, 16). For example, on the embodiment shown in FIGS. 6A and 6B, the nest 60 defined by the transducer support structure 18 helps ensure that a first electrical contact zone on the ultrasound transducer assembly 20 contacts the first contact portion 50 and that a second electrical contact zone on the ultrasound transducer assembly 20 contacts the second contact portion 52. By increasing the consistency of both the encapsulation process of the ultrasound transducer assembly 20 and the placement of the ultrasound transducer assembly, the use of the nest 60 defined by the transducer support structure 18 make the production of the ultrasound-enabled invasive medical device much more well-suited to automated production processes, such as an automated pick-and-place process. This helps increase the efficiency of production, which may help to provide both an increase in production throughput and/or a decrease in per-unit cost.

At optional step 112, an additional insulating layer may be deposited over the ultrasound-enabled invasive medical device after the ultrasound transducer assembly 20 has been attached. The insulating layer may be a vapor-deposited poly polymer, such as Parylene C or Polydimethylsiloxane (PDMS) for example. However, the insulating layer may be any other insulating material according to various embodiments. The insulating layer added during step 112 may be used to help the bio-compatibility of the ultrasound-enabled invasive medical device. Some materials used for the insulating layer, such as Parylene C, for example, may act as a moisture barrier as well as a dielectric.

In the embodiment described in FIGS. 2A-2F and FIGS. 4, 5A-5B, and 6A-6B, the needle 22 is shaped to define a flat surface 71 (see FIG. 5A) at the location where ultrasound transducer assembly 20 will be attached. The needle 22 may, for instance, be machined to form the flat surface 71 prior to depositing the insulating layer 26 during step 102. Other embodiments may not include the flat surface 71. For instance, a transducer support structure and the ultrasound transducer assembly may be mounted to an invasive medical device with a cross-section that is not flat. For example, the invasive medical device may have a round cross-section at the location where the transducer support structure and the ultrasound transducer assembly are mounted.

Figure 7A:
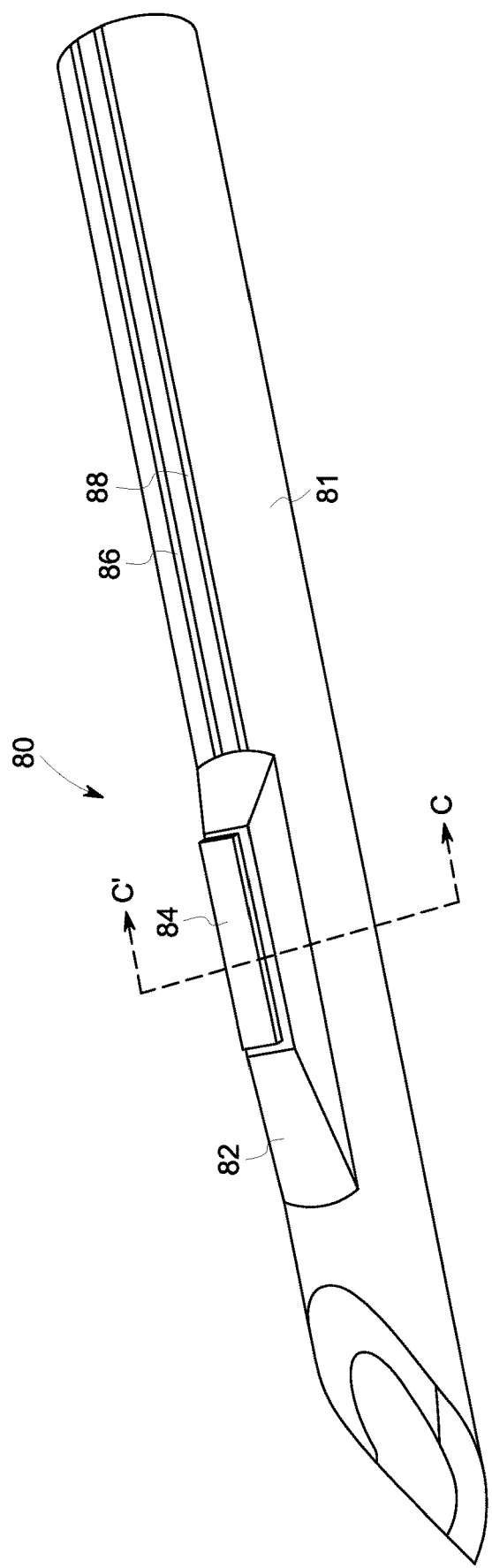
FIG. 7A is a perspective view of an ultrasound-enabled invasive medical device in accordance with an embodiment.
Figure 7B:
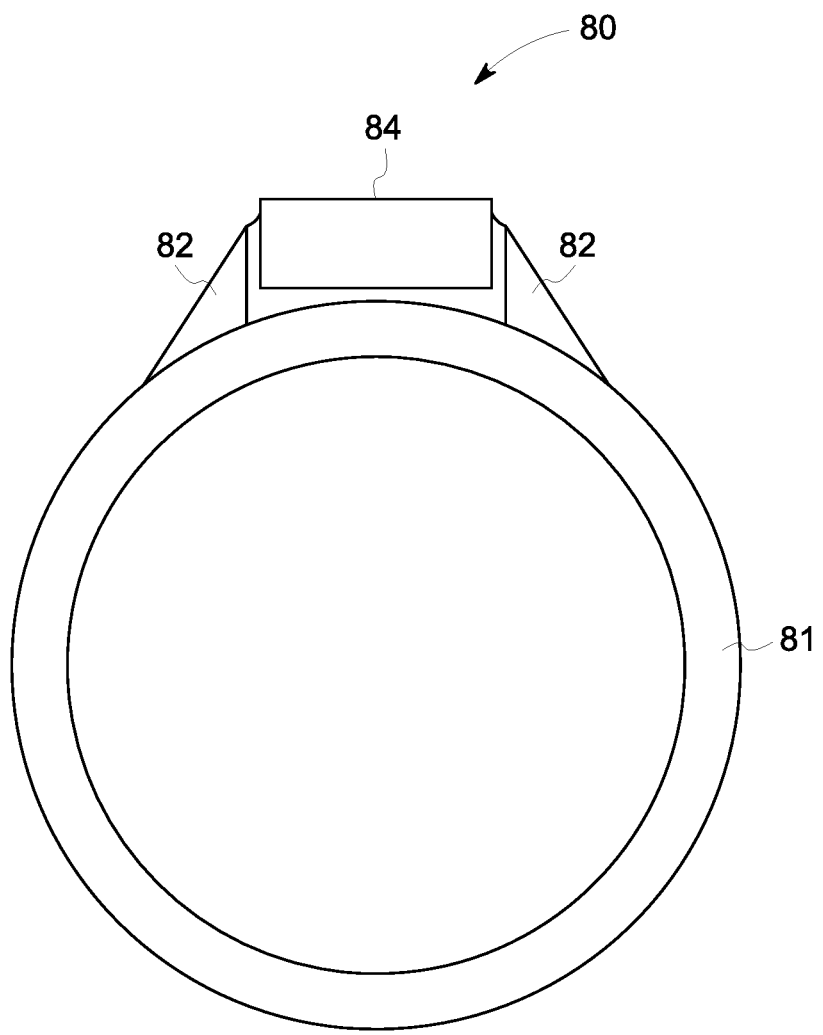
FIG. 7B is a sectional view of an ultrasound-enabled invasive medical device in accordance with an embodiment.

FIG. 7A is a perspective view of an ultrasound-enabled invasive medical device 80 in accordance with an embodiment. The ultrasound-enabled invasive medical device 80 includes a needle 81, a transducer support structure 82, the ultrasound transducer assembly 84, a first electrical trace 86 and the second electrical trace 88. The needle 81 is shaped to have a round cross-section at the location where the transducer support structure 82 and the ultrasound transducer assembly 84 are mounted. FIG. 7B is a sectional view of the ultrasound-enabled invasive medical device 80 along dashed line C-C'. In FIG. 7B, it is clearly apparent that the cross-section of the needle 23 is round at the location where the transducer support structure 14 and the ultrasound transducer assembly 20 are attached.

The transducer support structure 82 may be manufacture separately in a molding or micro-molding process, or the transducer support structure 82 may be deposited on the needle 81 in an additive manufacturing process, such as such as ink-jetting, aerosol jet printing or dispensing. Other than being curved in order to conform to a needle with a curved cross-section, the transducer support structure 82 otherwise functions identically to the transducer support structure 18 described with respect to previous embodiments. While the embodiment shown in FIGS. 7A and 7B has two electrical traces, other embodiment may have only a single electrical trace or more than 2 electrical traces. It should be appreciated by those skilled in that the number of individually controllable ultrasound transducer elements in the ultrasound transducer assembly 80 will dictate the number of electrical traces needed. As described hereinabove, each individually controllable ultrasound transducer element requires a conductive path for control signal and a separate conductive path for a ground return.

Figure 8A:
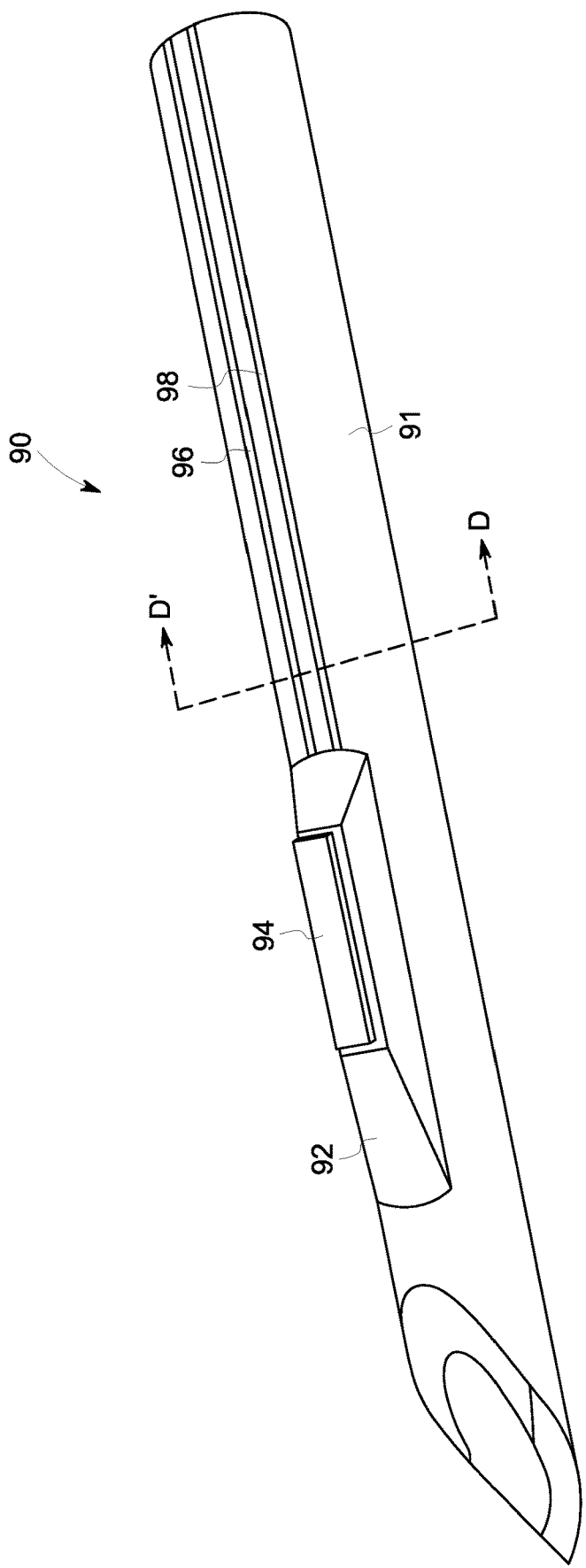
FIG. 8A is a perspective view of an ultrasound-enabled invasive medical device in accordance with an exemplary embodiment.

FIG. 8A is a perspective view of an ultrasound-enabled invasive medical device 90 in accordance with an exemplary embodiment. The ultrasound-enabled invasive medical device 90 includes a needle 91, an insulating layer 98, a first electrical trace 96, and a transducer support structure 92. The ultrasound transducer assembly 94 is a single-element array according to an embodiment. The first electrical trace 96 may be used to provide one of the control signal and the ground return for the ultrasound transducer assembly 94. The other of the control signal and the ground return is provided by the needle 91, which is made of a conductive material, such as steel. The insulating layer 98 electrically isolates the first electrical trace 96 from the conductive surface of the needle 91, thus enabling the needle 91 to function as an electrical pathway for the ultrasound-enabled invasive medical device 90.

Figure 8B:
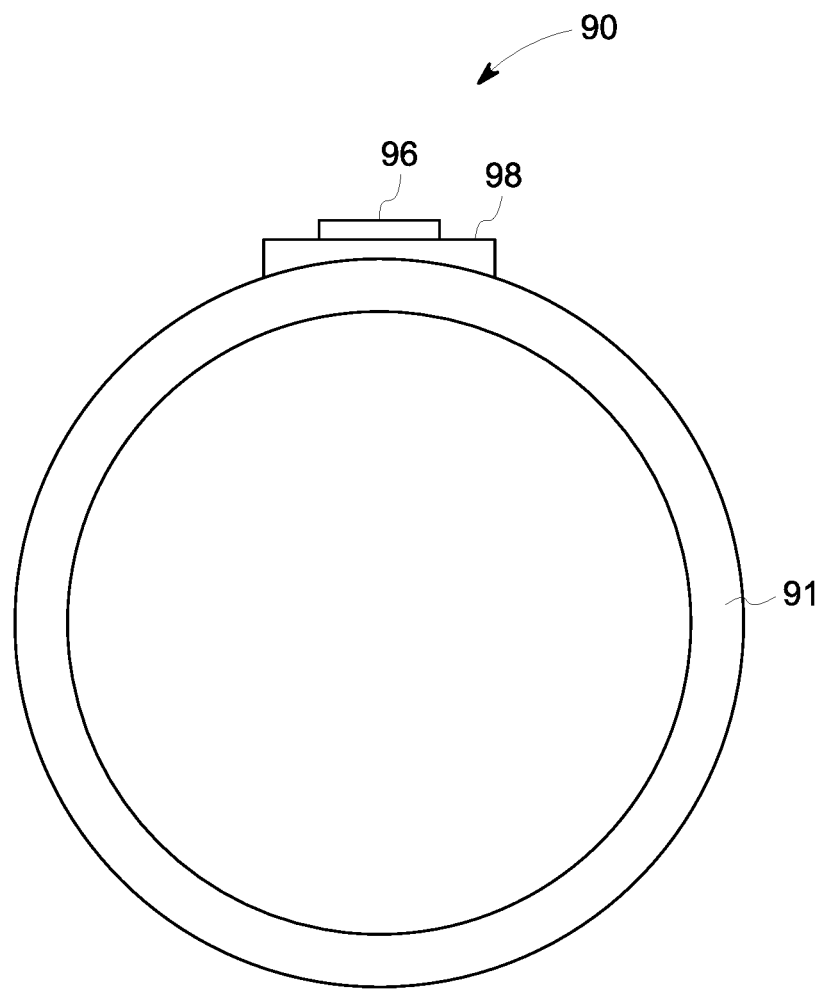
FIG. 8B is a sectional view of an ultrasound-enabled invasive medical device in accordance with an exemplary embodiment.

FIG. 8B is a sectional view of the ultrasound-enabled invasive medical device 80 along the dashed line D-D'. FIG. 8B shows a sectional view of the ultrasound-enabled invasive medical device 90. FIG. 8B clearly shows how the insulating layer 98 electrically isolates the first conductive path 96 from the needle 91. According to other embodiments, additional electrical traces may be deposited on the insulating layer. In other words, embodiments may use the needle as one conductive path while relying on two or more electrical traces for additional conductive paths in order to provide individual electrical connections for embodiments where the ultrasound transducer array 94 is a multi-element array with two or more ultrasound transducer elements.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:
1. An ultrasound-enabled invasive medical device comprising:
    an invasive medical device;
    an electrical trace deposited either directly onto a surface of the invasive medical device or onto an insulating layer covering at least a portion of the surface of the invasive medical device, wherein the electrical trace is deposited during an additive manufacturing process;
    an ultrasound transducer assembly attached to the invasive medical device and electrically connected to the electrical trace, wherein the ultrasound transducer assembly includes at least one ultrasound transducer element; and a transducer support structure attached to the invasive medical device and positioned over at least a portion of the electrical trace, wherein the transducer support structure defines a nest that is adapted to receive the ultrasound transducer assembly.

2. The ultrasound-enabled invasive medical device of claim 1, wherein the transducer support structure is fabricated via a molding process and laminated onto the invasive medical device.

3. The ultrasound-enabled invasive medical device of claim 1, wherein the transducer support structure is deposited onto the invasive medical device via an additional additive manufacturing process.

4. The ultrasound-enabled invasive medical device of claim 3, wherein the invasive medical device comprises a conductive portion, and wherein the electrical trace is deposited onto the insulating layer covering at least the portion of the surface of the invasive medical device, wherein the insulating layer electrically insulates the electrical trace from the conductive portion of the invasive medical device.

5. The ultrasound-enabled invasive medical device of claim 4, wherein the insulating layer is a vapor-deposited poly polymer.

6. The ultrasound-enabled invasive medical device of claim 3, wherein the invasive medical device is electrically conductive, and wherein the electrical trace is deposited onto the insulating layer covering at least the portion of the surface of the invasive medical device, wherein the insulating layer electrically insulates the electrical trace from the invasive medical device.

7. The ultrasound-enabled invasive medical device of claim 3, further comprising a second electrical trace deposited either directly onto the surface of the invasive medical device or onto the insulating layer covering at least the portion of the surface of the invasive medical device, wherein the second electrical trace is electrically connected to the ultrasound transducer assembly and wherein the second electrical trace is deposited during the additive manufacturing process.

8. The ultrasound-enabled invasive medical device of claim 7, wherein the invasive medical device is electrically conductive, and wherein the second electrical trace is deposited onto the insulating layer covering at least the portion of the surface of the invasive medical device.

9. The ultrasound-enabled invasive medical device of claim 7, wherein the invasive medical device is an electrical insulator, and wherein the second electrical trace is deposited directly onto the surface of the invasive medical device.

10. The ultrasound-enabled invasive medical device of claim 3, wherein the ultrasound transducer assembly is attached to the transducer support structure via an adhesive.

11. The ultrasound-enabled invasive medical device of claim 10, wherein a height of the transducer support structure is at least 80% of a height of the ultrasound transducer assembly when the ultrasound transducer assembly is attached to the transducer support structure via the adhesive.

12. The ultrasound-enabled invasive medical device of claim 1, wherein the ultrasound transducer assembly comprises a single-element array.

13. The ultrasound-enabled invasive medical device of claim 1, wherein the ultrasound transducer assembly comprises a multi-element array.

14. The ultrasound-enabled invasive medical device of claim 1, wherein the ultrasound transducer assembly comprises a transducer element selected from the group consisting of a capacitive micromachined ultrasonic transducer (CMUT) and a piezoelectric ultrasonic transducer.

15. The ultrasound-enabled invasive medical device of claim 1, wherein the invasive medical device is selected from the group consisting of catheter, an electrode, a stent, stylet, and a needle.

16. The ultrasound-enabled invasive medical device of claim 15, wherein the invasive medical device comprises the needle and wherein the ultrasound transducer assembly comprises a single-element array.

17. The ultrasound-enabled invasive medical device of claim 15, wherein the invasive medical device comprises the needle, wherein the electrical trace is deposited onto the insulating layer and the needle has a round cross-section where the ultrasound transducer assembly is attached to the needle.

18. The ultrasound-enabled invasive medical device of claim 15, wherein the invasive medical device comprises the needle, wherein the electrical trance is deposited onto the insulating layer and the needle is shaped to define a flat surface at the location where the ultrasound transducer assembly is attached to the needle.

19. The ultrasound-enabled invasive medical device of claim 1, further comprising a fiducial used to help position the transducer support structure with respect to the electrical trace.

20. The ultrasound-enabled invasive medical device of claim 19, wherein the electrical trace is shaped to define the fiducial.

21. The ultrasound-enabled invasive medical device of claim 1, wherein the ultrasound transducer assembly is configured to be used for one of guidance, therapy or imaging.

22. A method of manufacturing an ultrasound-enabled invasive medical device, the method comprising:

depositing an electrical trace either directly onto a surface of an invasive medical device or onto an insulating layer covering at least a portion of the surface of the invasive medical device, wherein said depositing the electrical trace is performed via an additive manufacturing process;

attaching a transducer support structure to the invasive medical device, wherein the transducer support structure is positioned over at least a portion of the electrical trace, wherein the transducer support structure defines a nest; and positioning an ultrasound transducer assembly within the nest defined by the transducer support structure and electrically connecting the ultrasound transducer assembly to the electrical trace, wherein the ultrasound transducer assembly includes at least one ultrasound transducer element.

23. The method of claim 22, further comprising fabricating the transducer support structure via a molding process and laminating the transducer support structure to the invasive medical device.

24. The method of claim 22, wherein said attaching the transducer support structure to the invasive medical device comprises depositing the transducer support structure via an additive manufacturing process.

25. The method of claim 22, further comprising:
applying the insulating layer to at least a portion of the surface of the invasive medical device; and
depositing the electrical trace onto the insulating layer.

26. The method of claim 22, further comprising applying an adhesive within the nest defined by the transducer support structure prior to positioning the ultrasound transducer assembly within the nest, wherein the adhesive is configured to attach the ultrasound transducer assembly to both the transducer support structure and the invasive medical device.

27. The method of claim 22, further comprising depositing, via the additive manufacturing process, a second electrical trace either directly onto the surface of an invasive medical device or onto the insulating layer covering at least a portion of the surface of the invasive medical device.

28. The method of claim 22, wherein the ultrasound transducer assembly comprises a single-element array.

29. The method of claim 22, wherein the ultrasound transducer assembly comprises a multi-element array.

30. The method of claim 22, wherein positioning the ultrasound transducer assembly within the nest is performed using a pick-and-place process.

31. The method of claim 30, wherein said positioning the ultrasound transducer assembly within the nest is performed as part of an automated process.

32. The method of claim 30, wherein said using the pick-and-place process comprises identifying a fiducial and using the fiducial to position the transducer support structure with respect to the electrical trace.

33. The method of claim 32, wherein the electrical trace is shaped to define the fiducial.

34. The method of claim 22, wherein the invasive medical device is selected from the group consisting of a catheter, an electrode, a stent, a stylet, and a needle.

\* \* \* \* \*